US012350049B2

(12) United States Patent
Jamal et al.

(10) Patent No.: US 12,350,049 B2
(45) Date of Patent: Jul. 8, 2025

(54) SMART URINE COLLECTION AND VOLUMETRIC MEASUREMENT APPARATUS

(71) Applicants: Mohammad Mazen Jamal, Irvine, CA (US); Roula Jamal, Irvine, CA (US)

(72) Inventors: Mohammad Mazen Jamal, Irvine, CA (US); Roula Jamal, Irvine, CA (US)

(*) Notice: Subject to any disclaimer, the term of this patent is extended or adjusted under 35 U.S.C. 154(b) by 0 days.

(21) Appl. No.: 17/693,366

(22) Filed: Mar. 13, 2022

(65) Prior Publication Data
US 2023/0284950 A1    Sep. 14, 2023

(51) Int. Cl.
*A61B 5/20*    (2006.01)
*A61B 5/00*    (2006.01)
*A61B 10/00*    (2006.01)

(52) U.S. Cl.
CPC .............. *A61B 5/208* (2013.01); *A61B 5/742* (2013.01); *A61B 10/007* (2013.01); *A61B 2560/0266* (2013.01); *A61B 2560/04* (2013.01); *A61B 2562/0271* (2013.01)

(58) Field of Classification Search
None
See application file for complete search history.

(56) References Cited

U.S. PATENT DOCUMENTS

| | | | | |
|---|---|---|---|---|
| 5,709,670 A | * | 1/1998 | Vancaillie | A61M 3/0233 604/246 |
| 2002/0116998 A1 | * | 8/2002 | Huss | G01F 23/247 73/295 |
| 2007/0022522 A1 | * | 2/2007 | Yu | A47K 13/24 4/237 |
| 2012/0310191 A1 | * | 12/2012 | LaVon | A61F 13/505 604/361 |
| 2017/0100068 A1 | * | 4/2017 | Kostov | A61M 39/28 |
| 2019/0365308 A1 | * | 12/2019 | Laing | G06F 9/542 |

OTHER PUBLICATIONS

Pereira et al. FBG-Based Temperature Sensors for Liquid Identification and Liquid Level Estimation via Random Forest, 2021 Sensors 2021, 21, 4568. (Year: 2021).*

* cited by examiner

*Primary Examiner* — Jay B Shah
(74) *Attorney, Agent, or Firm* — ARJOMAND LAW GROUP; Farjam Majd (57) ABSTRACT

A method and a device are disclosed including a urine collection device with sensors for determining the volume of the urine collected. A controller determines urine volume based on the height of sensors that show urine proximate to them within the device. A display indicates to the user whether the collected urine is sufficient for the required sample.

7 Claims, 5 Drawing Sheets

SMART URINE COLLECTION AND VOLUMETRIC MEASUREMENT APPARATUS

TECHNICAL FIELD

This application relates generally to medical sample equipment. More specifically, this application relates to a urine collector with volumetric measurement sensors.

BRIEF DESCRIPTION OF THE DRAWINGS

The drawings, when considered in connection with the following description, are presented for the purpose of facilitating an understanding of the subject matter sought to be protected.

DETAILED DESCRIPTION

While the present disclosure is described with reference to several illustrative embodiments described herein, it should be clear that the present disclosure should not be limited to such embodiments. Therefore, the description of the embodiments provided herein is illustrative of the present disclosure and should not limit the scope of the disclosure as claimed. In addition, while following description references the use of a device with a conventional toilet, it will be appreciated that the disclosure may be used in various clinical and diagnostic environments.

Briefly described, a urine collection device includes embedded sensors that detect the height of urine collected in the device. A controller in the collector determines, from the sensor data, the height of urine in the device and therefore the volume of urine collected. A display in the rim may communicate to a user whether the urine volume is sufficient or not.

In various embodiments, a urine collection device has a body having an internal volume for receiving urine. Sensors are each positioned at different vertical heights along the body. A controller receives data from the sensors and determines a volume of urine within the body of the urine collection device.

In various embodiments, a method of measuring a volume of urine within a collection device includes receiving data from sensors located at different heights. Sensors adjacent in height that provide different measurements are identified. The identified sensors are used to calculate a height for urine, which, along with the shape of the collection device, is used to determine a volume of urine.

In various embodiment, a urine collection device has a body, a rim, multiple sensor columns, and a controller. The body has an internal volume for receiving urine and at least one vertical wall. The rim is attached to and above the body and is substantially horizontal relative to the vertical orientation of the body. The sensor columns are within the vertical wall or walls of the body. Each column has multiple sensors, each at a different height. The controller is within the rim and receives data from each of the columns to determine a volume of urine within the body.

Figure 2A:
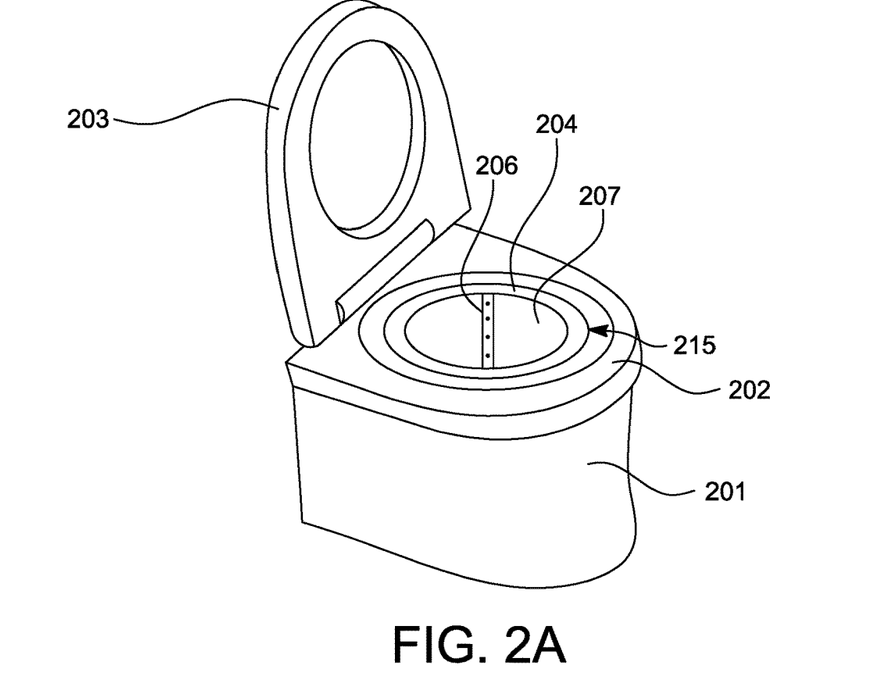
FIG. 2A shows an example of a urine collection device inserted into a toilet.
Figure 2B:
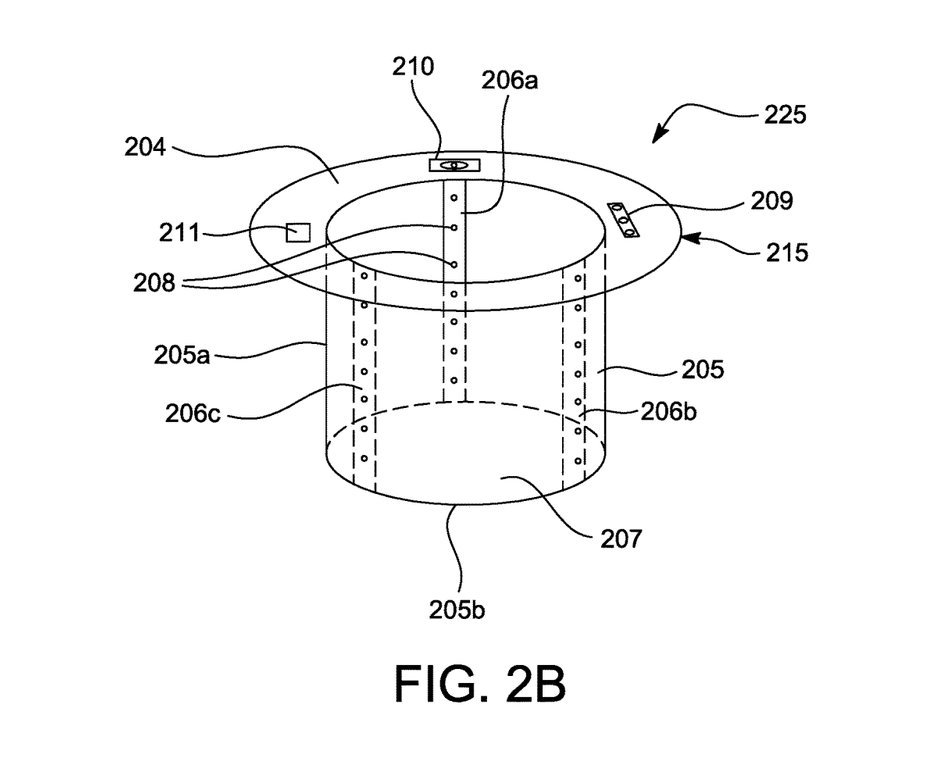
FIG. 2B shows a detailed view of the urine collection device of FIG. 2A.

It is to be noted that various orientations and directions, such as "up", "down", "inside", "outside", "top", "bottom", "exterior", "interior", and the like, are herein defined with respect to the rim 204 and open end of the urine collector as the top as shown in FIGS. 2A and 2B. The other orientations are defined accordingly.

Urinalysis is commonly used as a diagnostic aid. Most often, a subject is handed a small container with a line marking a minimum level at which it must be filled. Whether sufficient urine is collected is left to the judgment of attending nurses, physicians, or the subject (patient). If these actors misjudge the required level, it may be difficult to precure enough urine. This may compromise the tests being performed with the sample or require repeated sample collection.

Illustrative Operating Environment

Figure 1A:
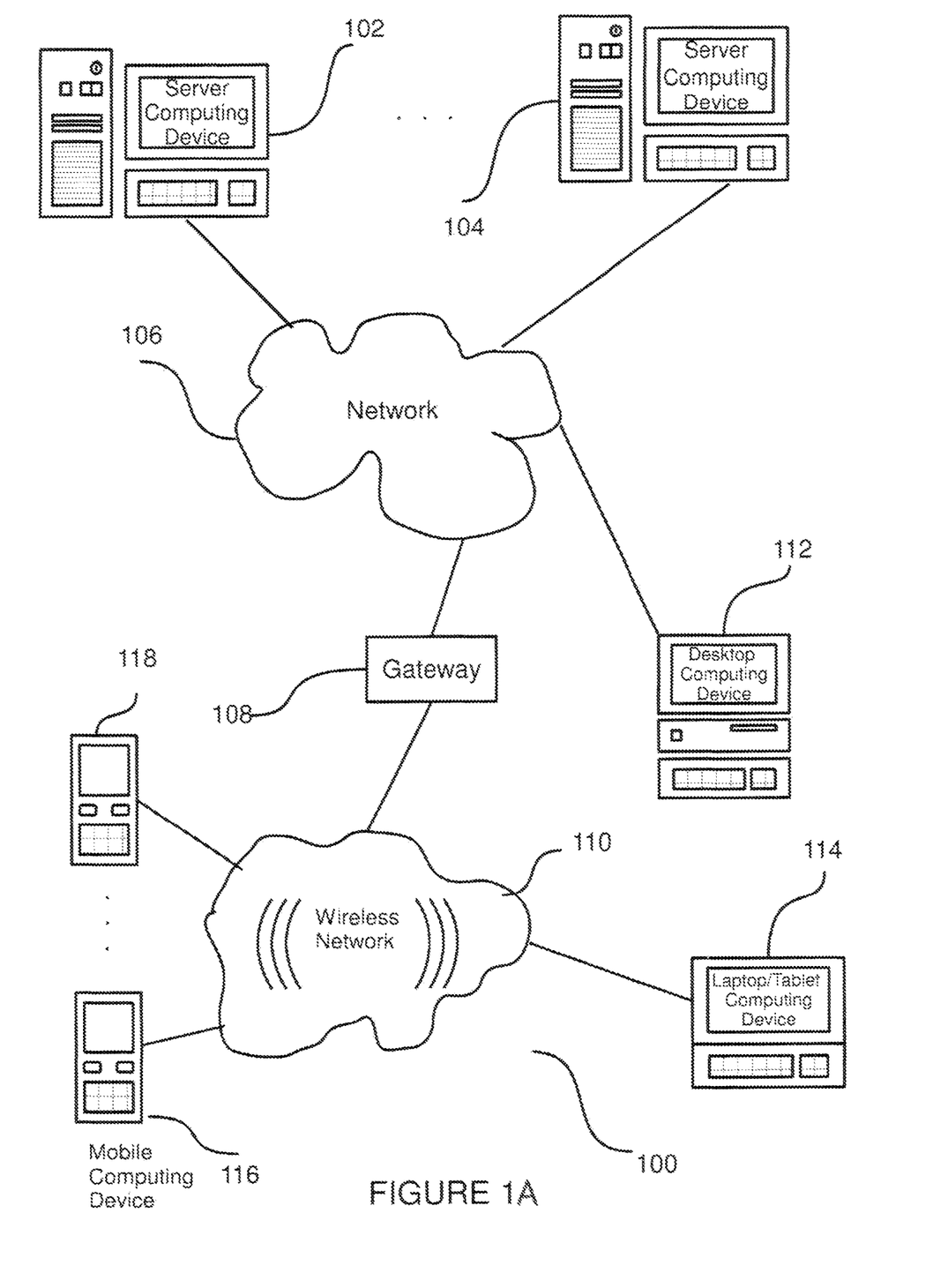
FIG. 1A shows an example network computing environment wherein the disclosure may be practiced.

FIG. 1A shows components of an illustrative environment in which the disclosure may be practiced. Not all the shown components may be required to practice the disclosure, and variations in the arrangement and type of the components may be made without departing from the spirit or scope of the disclosure. System 100 may include Local Area Networks (LAN) and Wide Area Networks (WAN) shown collectively as Network 106, wireless network 110, gateway 108 configured to connect remote and/or different types of networks together, client computing devices 112-118, and server computing devices 102-104.

One embodiment of a computing device usable as one of client computing devices 112-118 is described in more detail below with respect to FIG. 2. Briefly, however, client computing devices 112-118 may include virtually any device capable of receiving and sending a message over a network, such as wireless network 110, or the like. Such devices include portable devices such as, cellular telephones, smart phones, display pagers, radio frequency (RF) devices, music players, digital cameras, infrared (IR) devices, Personal Digital Assistants (PDAs), handheld computers, laptop computers, wearable computers, tablet computers, integrated devices combining one or more of the preceding devices, or the like. Client device 112 may include virtually any computing device that typically connects using a wired communications medium such as personal computers, multiprocessor systems, microprocessor-based or programmable consumer electronics, network PCs, or the like. In one embodiment, one or more of client devices 112-118 may also be configured to operate over a wired and/or a wireless network.

Client devices 112-118 typically range widely in terms of capabilities and features. For example, a cell phone may have a numeric keypad and a few lines of monochrome LCD display on which only text may be displayed. In another example, a web-enabled client device may have a touch sensitive screen, a stylus, and several lines of color LCD display in which both text and graphic may be displayed.

A web-enabled client device may include a browser application that is configured to receive and to send web pages, web-based messages, or the like. The browser application may be configured to receive and display graphic, text, multimedia, or the like, employing virtually any web based language, including a wireless application protocol messages (WAP), or the like. In one embodiment, the browser application may be enabled to employ one or more of Handheld Device Markup Language (HDML), Wireless Markup Language (WML), WMLScript, JavaScript, Standard Generalized Markup Language (SMGL), HyperText Markup Language (HTML), eXtensible Markup Language (XML), or the like, to display and send information.

Client computing devices 12-118 also may include at least one other client application that is configured to receive content from another computing device, including, without limit, server computing devices 102-104. The client application may include a capability to provide and receive textual content, multimedia information, or the like. The client application may further provide information that identifies itself, including a type, capability, name, or the like. In one embodiment, client devices 112-118 may uniquely identify themselves through any of a variety of mechanisms, including a phone number, Mobile Identification Number (MIN), an electronic serial number (ESN), mobile device identifier, network address, such as IP (Internet Protocol) address, Media Access Control (MAC) layer identifier, or other identifier. The identifier may be provided in a message, or the like, sent to another computing device.

Client computing devices 112-118 may also be configured to communicate a message, such as through email, Short Message Service (SMS), Multimedia Message Service (MMS), instant messaging (IM), internet relay chat (IRC), Mardam-Bey's IRC (mIRC), Jabber, or the like, to another computing device. However, the present disclosure is not limited to these message protocols, and virtually any other message protocol may be employed.

Client devices 112-118 may further be configured to include a client application that enables the user to log into a user account that may be managed by another computing device. Such user account, for example, may be configured to enable the user to receive emails, send/receive IM messages, SMS messages, access selected web pages, download scripts, applications, or a variety of other content, or perform a variety of other actions over a network. However, managing of messages or otherwise accessing and/or downloading content, may also be performed without logging into the user account. Thus, a user of client devices 112-118 may employ any of a variety of client applications to access content, read web pages, receive/send messages, or the like. In one embodiment, for example, the user may employ a browser or other client application to access a web page hosted by a Web server implemented as server computing device 102. In one embodiment, messages received by client computing devices 112-118 may be saved in non-volatile memory, such as flash and/or PCM, across communication sessions and/or between power cycles of client computing devices 112-118.

Wireless network 110 may be configured to couple client devices 114-118 to network 106. Wireless network 110 may include any of a variety of wireless sub-networks that may further overlay stand-alone ad-hoc networks, and the like, to provide an infrastructure-oriented connection for client devices 114-118. Such sub-networks may include mesh networks, Wireless LAN (WLAN) networks, cellular networks, and the like. Wireless network 110 may further include an autonomous system of terminals, gateways, routers, and the like connected by wireless radio links, and the like. These connectors may be configured to move freely and randomly and organize themselves arbitrarily, such that the topology of wireless network 110 may change rapidly.

Wireless network 110 may further employ a plurality of access technologies including 2nd (2G), 3rd (3G) generation radio access for cellular systems, WLAN, Wireless Router (WR) mesh, and the like. Access technologies such as 2G, 3G, and future access networks may enable wide area coverage for mobile devices, such as client devices 114-118 with various degrees of mobility. For example, wireless network 110 may enable a radio connection through a radio network access such as Global System for Mobil communication (GSM), General Packet Radio Services (GPRS), Enhanced Data GSM Environment (EDGE), WEDGE, Bluetooth, Bluetooth Low Energy (LE), High Speed Downlink Packet Access (HSDPA), Universal Mobile Telecommunications System (UMTS), Wi-Fi, Zigbee, Wideband Code Division Multiple Access (WCDMA), and the like. In essence, wireless network 110 may include virtually any wireless communication mechanism by which information may travel between client devices 102-104 and another computing device, network, and the like.

Network 106 is configured to couple one or more servers depicted in FIG. 1A as server computing devices 102-104 and their respective components with other computing devices, such as client device 112, and through wireless network 110 to client devices 114-118. Network 106 is enabled to employ any form of computer readable media for communicating information from one electronic device to another. Also, network 106 may include the Internet in addition to local area networks (LANs), wide area networks (WANs), direct connections, such as through a universal serial bus (USB) port, other forms of computer-readable media, or any combination thereof. On an interconnected set of LANs, including those based on differing architectures and protocols, a router acts as a link between LANs, enabling messages to be sent from one to another.

In various embodiments, the arrangement of system 100 includes components that may be used in and constitute various networked architectures. Such architectures may include peer-to-peer, client-server, two-tier, three-tier, or other multi-tier (n-tier) architectures, MVC (Model-View-Controller), and MVP (Model-View-Presenter) architectures among others. Each of these are briefly described below.

Peer to peer architecture entails use of protocols, such as P2PP (Peer To Peer Protocol), for collaborative, often symmetrical, and independent communication and data transfer between peer client computers without the use of a central server or related protocols.

Client-server architectures includes one or more servers and a number of clients which connect and communicate with the servers via certain predetermined protocols. For example, a client computer connecting to a web server via a browser and related protocols, such as HTTP, may be an example of a client-server architecture. The client-server architecture may also be viewed as a 2-tier architecture.

Two-tier, three-tier, and generally, n-tier architectures are those which separate and isolate distinct functions from each other by the use of well-defined hardware and/or software boundaries. An example of the two-tier architecture is the client-server architecture as already mentioned. In a 2-tier architecture, the presentation layer (or tier), which provides user interface, is separated from the data layer (or tier), which provides data contents. Business logic, which processes the data may be distributed between the two tiers.

A three-tier architecture, goes one step farther than the 2-tier architecture, in that it also provides a logic tier between the presentation tier and data tier to handle application data processing and logic. Business applications often fall in and are implemented in this layer.

MVC (Model-View-Controller) is a conceptually many-to-many architecture where the model, the view, and the controller entities may communicate directly with each other. This is in contrast with the 3-tier architecture in which only adjacent layers may communicate directly.

MVP (Model-View-Presenter) is a modification of the MVC model, in which the presenter entity is analogous to the middle layer of the 3-tier architecture and includes the applications and logic.

Communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communications links known to those skilled in the art. Furthermore, remote computers and other related electronic devices could be remotely connected to either LANs or WANs via a modem and temporary telephone link. Network 106 may include any communication method by which information may travel between computing devices. Additionally, communication media typically may enable transmission of computer-readable instructions, data structures, program modules, or other types of content, virtually without limit. By way of example, communication media includes wired media such as twisted pair, coaxial cable, fiber optics, wave guides, and other wired media and wireless media such as acoustic, RF, infrared, and other wireless media.

In various embodiments, the client computing devices 112-118, the networks 106 and 110, and server computing devices 102 and 104 may operate in real-time. As generally known in the relevant computing arts, the term "real-time" may mean one or more of several operating characteristics. One aspect of real-time is having computing deadlines, often measured in milliseconds or microseconds, by which a task must be completed. For example, with a deadline of 4 milliseconds from request time, fetching a data record from a database in under 4 milliseconds satisfies the deadline, and hence, would be considered as real-time performance in the particular case so defined. Another aspect of real-time computing is that data at one location in memory, storage, display, or record is updated by a computing device at substantially the same rate as new data is received by the computing device from other sources. For example, if financial stock information is received by a computing device at a particular rate, such as 10 data records per second, then if the display of such data is also updated at the same rate on a display screen, then the real-time requirement would be considered as satisfied. Yet another aspect of real-time computing is the control of a process, physical or virtual (software process), in which data or signals processed and/or provided by a computing device must reach the process before a particular step in the process is over and terminated. For example, if a computing device in a car, such as a microcontroller, is controlling the engine gas intake via the fuel injector, the signal cannot reach the fuel injector after the engine gas intake valve is closed. The signal must reach the fuel injector before the step of gas intake in the engine working cycle is completed to control flow of gas into the engine. In this aspect, the deadline for computing is set by the duration of a process step, not by a fixed time constant.

Illustrative Computing Device Configuration

Figure 1B:
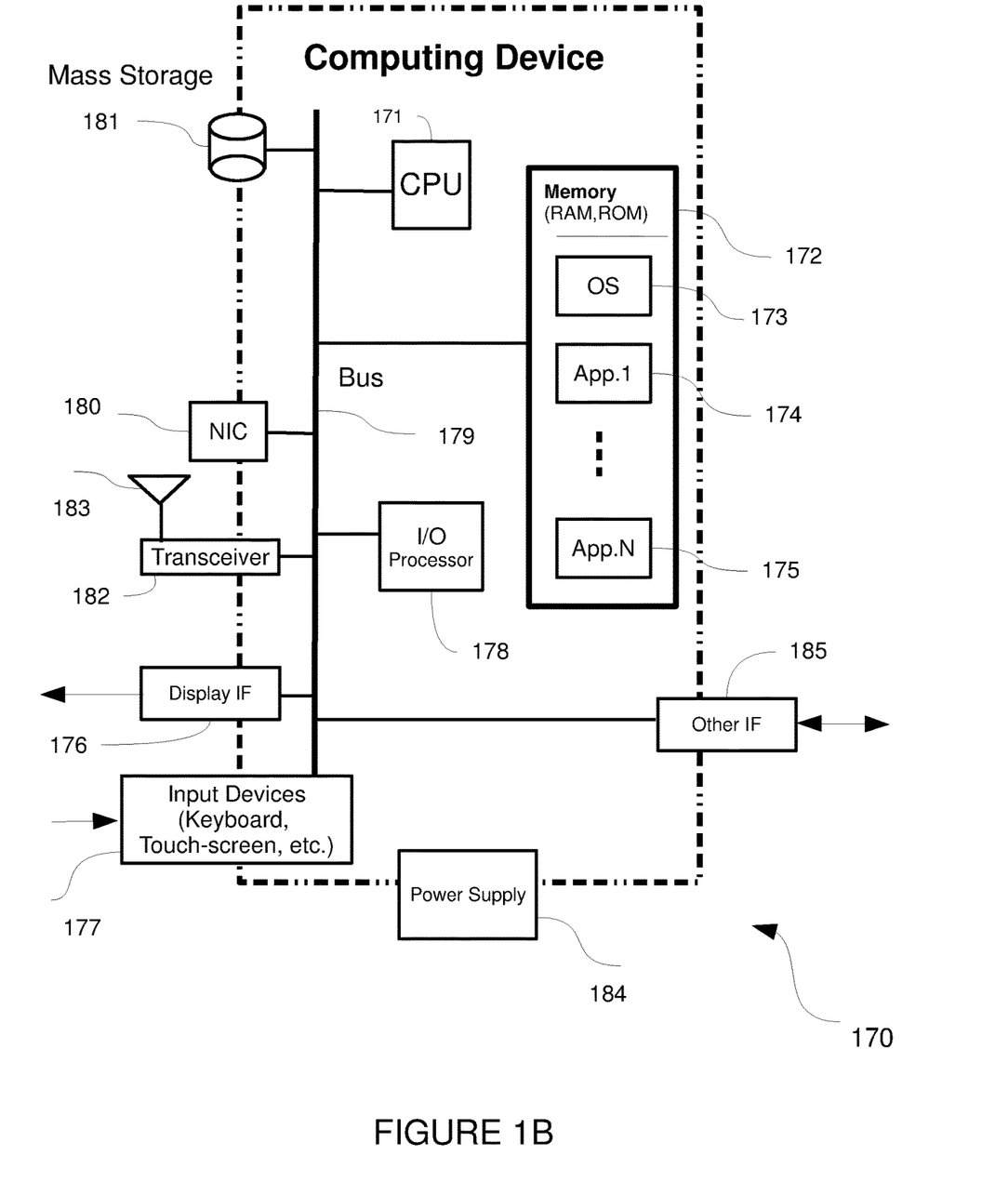
FIG. 1B shows an example computing device that may be used in the network computing environment of FIG. 1A.

FIG. 1B shows an illustrative computing device 170 that may represent any type of mobile, desktop, or server computer or embedded microcontroller. A computing device represented by computing device 170 may include less or more than all the components shown in FIG. 1B depending on the functionality needed. For example, a mobile computing device may include the transceiver 182 and antenna 183, while a server computing device may not include these components. Those skilled in the art will appreciate that the scope of integration of components of computing device 170 may be different from what is shown. As such, some of the components of computing device 170 shown in FIG. 1B may be integrated together as one unit. For example, Network Interface Card (NIC) 180 and transceiver 182 may be implemented as an integrated unit. Additionally, different functions of a single component may be separated and implemented across several components instead. For example, different functions of I/O processor 178 may be separated into two or more processing units.

With continued reference to FIG. 1B, computing device 170 includes mass storage 181, Central Processing Unit (CPU) 171, memory module 172, display interface 185, input devices 177, Input/Output (I/O) processor 178, bus 179, various other interfaces 185, NIC 180, power supply 184, transceiver 182, and antenna 183, all interconnected for electronic communication via data and/or control and/or address bus 179, Memory module 172 may include software such as Operating System (OS) 173, and a variety of software application programs and/or software modules/components 174-175. Such software modules and components may be stand-alone application software or be components, such as DLL (Dynamic Link Library) of a bigger application software. Computing device 170 may also include other components not shown in FIG. 1B. For example, computing device 170 may further include an illuminator (for example, a light), graphic interface, and portable storage media such as USB drives. Computing device 170 may also include other processing units, such as a math co-processor, graphics processor/accelerator, and a Digital Signal Processor (DSP).

Mass storage device 181 may include magnetic disks, magnetic tapes, optical drives for using optical media, such as CD (Compact Disc), DVD (Digital Video Disc), and the like. Mass storage devices 181 may provide large data and software storage as well inexpensive ways for storing information for archival and/or distribution purposes. In various embodiments, mass storage 181 may be a hard disk having a Ferro-magnetic stack of one or more disks forming a disk drive embedded in or coupled to computing device 170. A hard disk may be implemented as a solid-state device configured to behave as a disk drive, such as a flash-based hard drive. The mass storage device 181 may be a remote storage accessible over network interface 180 or another interface 185, but acting as a local hard drive. Those skilled in the art will appreciate that other technologies and configurations may be used to present a hard drive interface and functionality to computing device 170 without departing from the spirit of the present disclosure. In some embodiments, the mass storage devices may include USB (Universal Serial Bus) drives that may be implemented by PCM (Phase Change Memory) arrays, flash memory including NOR and NAND flash, pluggable hard drive, and the like.

Central Processing Unit (CPU) 171 may be the main processor for software program execution in computing device 170. CPU 171 may represent one or more processing units that obtain software instructions from memory module 172 and execute such instructions to carry out computations and/or transfer data between various sources and destinations of data, such as mass storage devices 181, I/O processor 178, display interface 176, input devices 177, and the like.

Memory module 172 may include RAM (Random Access Memory), ROM (Read Only Memory), and other storage means, mapped to one addressable memory space. Memory module 106 illustrates one of many types of computer storage media for storage of information such as computer readable instructions, data structures, program modules or other data. Memory module 172 may store a Basic Input/Output System (BIOS) for controlling low-level operation of computing device 170. Memory module 172 may also store OS 173 for controlling the general operation of computing device 170. The OS 173 may include a general-purpose operating system such as a version of UNIX, or LINUX™, or a specialized client-side and/or mobile communication operating system such as Windows Mobile™, Android®, or the Symbian® operating system.

Memory module 106 may further include one or more distinct areas (by address space and/or other means), which can be utilized by computing device 170 to store, among other things, applications and/or other data. For example, one area of memory module 172 may be set aside and employed to store information that describes various capabilities of computing device 170, a device identifier, and the like. Such identification information may then be provided to another device based on any of a variety of events, including being sent as part of a header during a communication, sent upon request, or the like. One common software application is a browser program that is generally used to send/receive information to/from a web server. In one embodiment, the browser application is enabled to employ Handheld Device Markup Language (HDML), Wireless Markup Language (WML), WMLScript, JavaScript, Standard Generalized Markup Language (SMGL), HyperText Markup Language (HTML), eXtensible Markup Language (XML), and the like, to display and send a message. However, any of a variety of other web based languages may also be employed.

Display interface 176 may be coupled with a display unit (not shown), such as liquid crystal display (LCD), gas plasma, light emitting diode (LED), or any other type of display unit that may be used with computing device 100. Display units coupled with display interface 176 may also include a touch sensitive screen arranged to receive input from an object such as a stylus or a digit from a human hand. Display interface 176 may further include interface for other visual status indicators, such Light Emitting Diodes (LED), light arrays, and the like. Display interface 176 may include both hardware and software components. For example, display interface 176 may include a graphic accelerator for rendering graphic-intensive outputs on the display unit. In one embodiment, display interface 176 may include software and/or firmware components that work in conjunction with CPU 171 to render graphic output on the display unit.

Input devices 177 may include a variety of device types arranged to receive input from a user, such as a keyboard, a keypad, a mouse, a touchpad, a touch-screen (described with respect to display interface 176), a multi-touch screen, a microphone for spoken command input (for use with an audio interface), and the like.

I/O processor 178 is generally employed to handle transactions and communications with peripheral devices such as mass storage, network, input devices, display, and the like, which couple computing device 170 with the external world. In small, low power computing devices, such as some mobile devices, functions of the I/O processor 178 may be integrated with CPU 171 to reduce hardware cost and complexity. In one embodiment, I/O processor 178 may the primary software interface with all other device and/or hardware interfaces, such as mass storage 181, other interfaces 185, display interface 176, and input devices 177.

An electrical bus 179 internal to computing device 170 may be used to couple various other hardware components, such as CPU 171, memory module 172, I/O processor 178, and the like, to each other for internally specifying memory and register addresses for transferring data, instructions, status, and other similar information to the specified addresses.

Various other interfaces 185 may include other electrical and/or optical interfaces for connecting to various hardware peripheral devices and networks, such as speakers and microphones for audio interface, GPS (Global Positioning System), IEEE 1394 also known as FireWire, Universal Serial Bus (USB), Small Computer Serial Interface (SCSI), parallel printer interface, Universal Synchronous Asynchronous Receiver Transmitter (USART), Video Graphics Array (VGA), Super VGA (SVGA), and the like.

NIC 180 may include circuitry for coupling computing device 100 to one or more networks, and is generally constructed for use with one or more communication protocols and technologies including, but not limited to, Global System for Mobile communication (GSM), code division multiple access (CDMA), time division multiple access (TDMA), user datagram protocol (UDP), transmission control protocol/Internet protocol (TCP/IP), SMS, general packet radio service (GPRS), WAP, ultra wide band (UWB), IEEE 802.16 Worldwide Interoperability for Microwave Access (WiMax), SIP/RTP, Bluetooth, Wi-Fi, Zigbee, UMTS, HSDPA, WCDMA, WEDGE, or any of a variety of other wired and/or wireless communication protocols.

Power supply 184 provides power to computing device 170. A rechargeable or non-rechargeable battery may be used to provide power. The power may also be provided by an external power source, such as an AC adapter or a powered docking cradle that supplements and/or recharges a battery.

Transceiver 182 generally represents transmitter/receiver circuits for wired and/or wireless transmission and receipt of electronic data. Transceiver 182 may be a stand-alone module or be integrated with other modules, such as NIC 180, GPS hardware that may be part of the computing device. Transceiver 182 may be coupled with one or more antennas for wireless transmission of information.

Antenna 183 is generally used for wireless transmission of information, for example, in conjunction with transceiver 182, NIC 180, and a GPS unit of the computing device. Antenna 183 may represent one or more different antennas that may be coupled with different devices and tuned to different carrier frequencies configured to communicate using corresponding protocols and/or networks. Antenna 183 may be of various types, such as omni-directional, dipole, slot, helical, and the like.

FIG. 2A shows an example of a urine collector inserted into a toilet. In various embodiments, the urine collection arrangement 200 includes a urine collection device 215 having a rim 204, body 205, and a sensor column 206. The urine collection device 215 is placed in a toilet 201, which includes a porcelain base 202 and a seat 203.

Toilet 201 is not itself part of the urine collection device 215, but instead illustrates one environment in which the urine collection device 215 can be used. The shape of the body 205 allows it to be placed within the porcelain base 202 of the toilet 201 with the rim 204 under the toilet seat 203. Many other environments may be appropriate for the use of urine collection device 215, and in different implementations, the device body 205 may be shaped differently for different environments.

FIG. 2B shows a detailed view of the urine collector of FIG. 2A. In various embodiments, the urine collection device configuration 225 may include rim 204, body 205 with side wall 205*a* and floor (or bottom) 205*b*, sensor columns 206a, 206b, and 206c, internal space 207, sensors 208, display 209, level 210, and controller 211.

In various embodiments, the rim 204 and body 205 may be made of any appropriate material, such as medical-grade plastic. The material for the body 205 may be conductive to changes in temperature (for use of the sensor columns as further described below), water-impermeable, and non-reactive with substances such as uric acid that are typically found in human waste.

In various embodiments, the body 205 is composed of a side wall 205a and a floor 205b. As shown, the side wall 205a may be substantially vertical and the floor 205b substantially horizontal so that urine collects within the body 205 by filling from the floor up. In this way, the body 205 defines a vertical orientation for the urine collection device 215 in which towards the floor 205b is "down" and towards the rim 204 is "up," with the "height" of elements of the urine collection device 215 being defined relative to the vertical position of the floor 205b.

In various embodiments, one or more, for example three as shown in FIG. 2B, sensor columns 206a, 206b, and 206c may each be located within the side wall 205a at different radial locations. Each sensor column may also include multiple sensors which are lined up to be directly above each other at different heights. In the illustrated embodiment of FIG. 2B, the heights of the sensors are evenly distributed, but the height distribution may vary in other embodiments.

In various embodiments, the sensor columns 206a-c may include sensors of a variety of types for sensing urine. In one embodiment, the sensors may be temperature sensors. In another environment, the sensors may be urea sensors. Still in other embodiments, the sensors may be water or fluid or humidity sensors. In some embodiments, apertures may be deployed in the side wall 205a or on sensor columns 206a-c, to couple with sensors and allow fluid to come in physical contact with fluid or other types of sensors. It will also be recognized that different sensor types may be used in the same embodiment, such as alternating between chemical and temperature sensors, or having all of the sensors of a particular column be of the same type but the sensor type of one column being different than another column.

Other details of the urine collection device 215 may depend on the nature of the sensors 208 For example, where sensors 208 are temperature sensors, which are installed and used on the exterior of the vertical wall 205a, the wall 205a may be an unbroken thin surface to allow relatively quick heat transfer to sensors compared with a thicker surface (??Explain??). The sensors may detect a change of temperature through the surface of the wall 205a. Where the sensor requires contact with the liquid to be sensed, apertures that a coupled with sensors 208 may be included in the vertical wall 205a adjacent to each sensor.

The vertical wall 205a and floor 205b collectively enclose an internal space 207 in which urine is collected. The volume of the internal space 207 depends on the shape and size of the body 205, and may vary depending on the nature of the environment in which the urine collection device 215 is to be used.

In various embodiments, sensors 208 and/or sensor columns 206a-c are in communication with controller 211. The communication may be performed by passing electrical signals representing sensor measurement data between the sensors 208 and the controller 211. The electrical signals (data) may be transmitted via wired connections or wireless connections using various appropriate protocols, as described with respect to FIG. 1B. Signals from the sensor columns 206a-c may be received by the controller 211 embedded within the device rim 204, or within other parts of the urine collection device 215. In some embodiments, the controller 211 may send control or configuration signals to the sensors, that may configure the sensors in various ways, such as turning sensors ON or OFF, resetting sensors, calibrating sensors, polling the sensors to read data in a particular order or sequence, or performing multiple data-read operations to confirm the data before processing and diagnosis, and the like. The controller 211 may be include elements of the computing device described above and depicted in FIG. 1B. As noted above, signals may be transmitted wirelessly from the sensors or by wires embedded within the urine collection device 215. If the controller 211 is vulnerable to contamination by liquids, the controller 211 may be sealed within the material of the rim 204. As further described below with respect to FIG. 3, the controller 211 determines a urine volume level within the interior space 207 using the received sensor data.

In various embodiments, the controller 211 may further communicate, by wire or wirelessly, with a central computer system to upload data for permanent storage in a patient's medical records, and/or to download various instructions and information from the central computer system for configuration of the controller 211, sensors 208, and display 209.

In various embodiments, a display 209 may be embedded in the rim 204. In some implementations, the display may be removable; it may also receive wireless signals or may be attached by wires disposed within the urine collection device 215. In various embodiments, the display 209 may be a set of light emitting diodes (LED) or other similar indicators, while in other embodiments, the display 209 may be an alphanumeric character or graphic display. The display 209 may be controlled by the controller. In some embodiments, the display 209 provides instructions to a user on how to deploy the collection device. Once the controller 211 determines that urine has entered the interior space 207, the display 209 may provide an indication of the urine volume as a continuously changing number. A numerical value may be displayed, or a more general indicator may represent either that the volume is sufficient or not. In some implementations, further instructions may be provided by the display if an insufficient amount of urine is detected.

In various embodiments, a level 210 embedded in the rim 204 that allows the user to assure that the device 204 is oriented correctly (for example, horizontally with respect to gravitational force) prior to collection. In some implementations, the level 210 may be a purely mechanical device such as a bubble level. The level may, in some embodiments, include one or more electrical components allowing it to send data to the controller 211. When data from the level 210 is sent to the controller 211, that data may be used by the controller to determine if the urine collection device 215 is oriented properly for use. The data from the level 210, in conjunction with the sensors 208 data, may also be used when determining a volume of urine within the interior space 207.

Figure 2C:
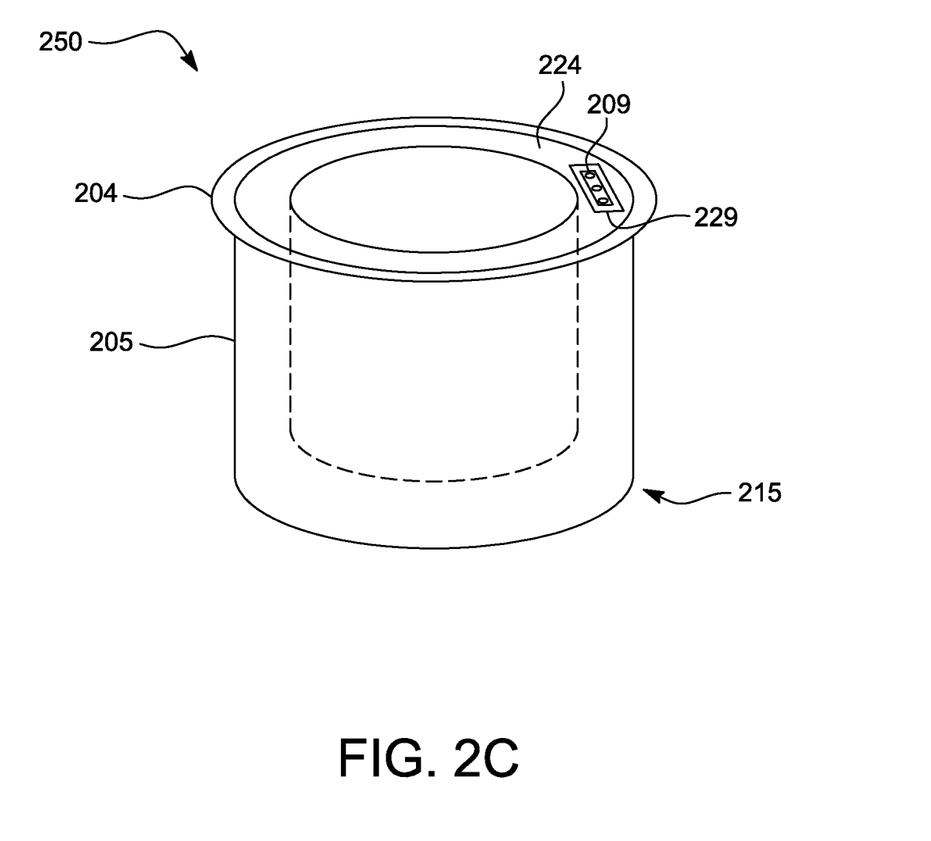
FIG. 2C shows an example insert or liner useable with the urine collection device of FIG. 2A.

FIG. 2C shows an example insert or liner useable with the urine collection device of FIG. 2A. In various embodiments, insert arrangement 250 may include an insert 220 that may be added to the urine collection device 215. The insert 220 may be overlaid on the rim 204 and body 205 of the urine collection device 215 during urine collection. The insert rim 224 may include a window 229 so that the display 209 is visible when the insert 220 is placed. The insert 220 may be more easily washable than the urine collection device 215 or may be a disposable liner. The insert 220 may be made of material with good thermal conductivity so that the sensor columns 206a-c can accurately detect heat from urine through the walls of the insert 220.

In various embodiments, insert 220 may be made of thin plastic, polyester, resin-impregnated membrane, or other thin material that has low cost and is a good conductor of heat. The use of an insert or liner in the urine collection device allows quick application and easy cleanup after urine collection from a patient.

Figure 3:
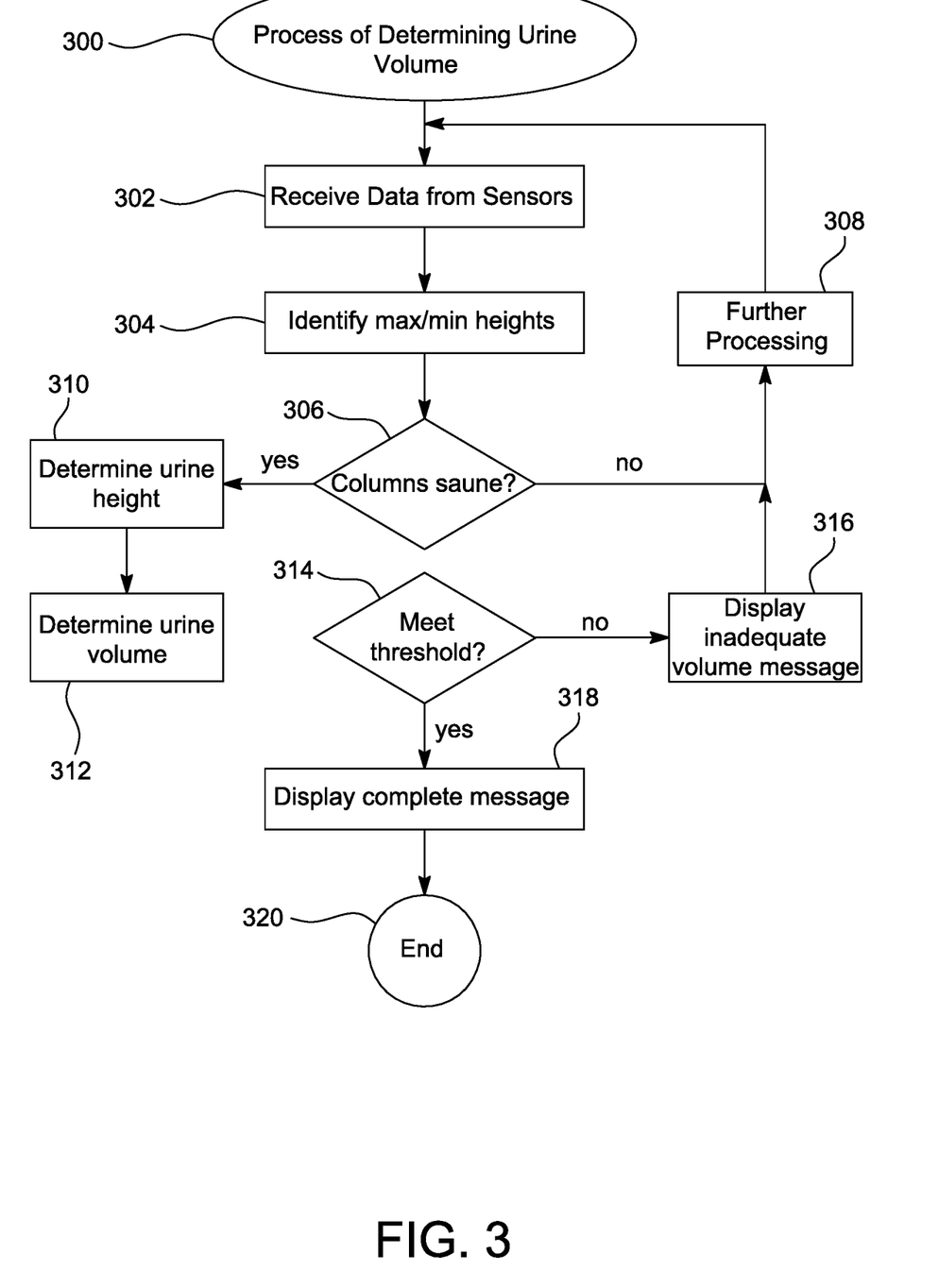
FIG. 3 shows an example flow diagram of the process of determining a volume of urine using the device as described.

FIG. 3 shows an example flow diagram of the process of determining a volume of urine using the device as described.

The controller 211 may receive data from multiple sensors 302. Table 1 below gives an example of sensor readings from three groups (columns A, B, and C in table below) of sensors arranged vertically along the wall 205a of the urine collection device 215. In various embodiments, the controller 211 may process such data according to the method of determining urine volume 300.

| Sensor Height Along Wall 205a | Column-A Sensors' Readings | Column-B Sensors' Readings | Column-C Sensors' Readings |
|---|---|---|---|
| 1 cm | 36.6 | 36.8 | 37.0 |
| 2 cm | 36.4 | 37.1 | 37.1 |
| 3 cm | 37.0 | 35.5 | 37.2 |
| 4 cm | 22.2 | 20.1 | 20.4 |
| 5 cm | 20.1 | 19.9 | 19.8 |
| 6 cm | 20.0 | 20.2 | 20.3 |
| 7 cm | 22.8 | 23.4 | 20.7 |

The method of determining urine volume 300 based on sensor data proceeds to block 302, where sensor data are received via wired or wireless data transmission by the controller 211. In various embodiments, as described with respect to FIG. 2, the controller 211 may have some or all of the components of the computing device 170, such as CPU, memory, transceivers for data communications, and the like. The data are received by controller 211 via its transceivers and stored in memory for further processing. The process proceeds to block 304.

At block 304, the controller 211 identifies, for each column, a maximum height associated with body temperature and a minimum height associated with room temperature. From the example data of Table 1, the maximum height associated with body temperature (approximately 37° C.) is 3 cm in each column, while the minimum height associated with room temperature (approximately 20° C.) is 4 cm in each column. The process proceeds to decision block 306.

At decision block 306, controller 211 compares the data in each column to see if they are the same. The sensor data are considered to be the same if corresponding sensors (that is, sensors at the same height) in different columns indicate urine level has reached them. If the sensor data are not the same the controller may perform further data collection to reconcile the difference (see block 308), such as averaging the different heights data or taking multiple readings from the same sensors to compare over an interval of time. The process proceeds to block 308 if no decision can be made (data are not the same) based on current data, or proceeds to block 310 if a decision can be made (data are the same).

At block 308, it has been determined that more data is needed from the sensors to make a decision about urine level. Multiple data from various sensors in different columns at same height along the urine collection device may be averaged over space (that is, collection is done at the same time but at different locations for the columns) to arrive at a urine level determination. Multiple readings may also be obtained over time and averaged (that is, collection is done at the same location but at different times, such as four times a second). The data averaging over time and space may also be combined to obtain a final value for urine level. Other decision methods, such as voting algorithms, may also be used. In a voting algorithm, when multiple sources of the same data are employed, which may yield inconsistent data, the data value consistent with the majority or most of the data sources is selected. The process proceeds to block 302.

At block 310, controller 211 determines the height of urine in the urine collection device 215 based on the sensors which have detected urine at their levels. The urine level height is determined as being at the highest sensor level with respect to the bottom of the urine collection device 215. The urine volume is then determined based on the predetermined geometry of the urine collection device 215. For example, if the urine collection device 215 is cylindrical, then the volume is determined by multiplying the urine level height by the base area (area of the bottom) of the urine collection device 215. More specifically, using the example of Table 1, if the interior space of the urine collection device 215 is cylindrical with a base area of 17 $cm^2$, then from a determined height of 3 cm [use passive case, never first or second person statements like "we can" or "you can" ] the urine volume may be determined to be 51 mL. The process proceeds to decision block 314.

At decision block 314, the urine level height determined at block 310 is compared with a predetermined threshold to determine if sufficient urine has been collected for medical purposes. This threshold is predetermined and programmed into the controller 211. If the amount of urine is sufficient, the process proceeds to block 318. If the amount of urine is insufficient, the process proceeds to block 316.

At block 316, a message is displayed to the user and/or attending medical staff on the display 209 that the amount of urine is insufficient. This message indicates to the patient that more urine needs to be collected. The process proceeds to block 302.

At block 318, a message is displayed to the user and/or attending medical staff on the display 209 that the amount of urine is sufficient. This message indicates to the patient that the urine collection process is completed. The process proceeds to block 320.

At block 320, the method terminates.

It will be understood that unless explicitly stated or specified, the steps described in a process are not ordered and may not necessarily be performed or occur in the order described or depicted. For example, a step A in a process described prior to a step B in the same process, may actually be performed after step B. In other words, a collection of steps in a process for achieving an end-result may occur in any order unless otherwise stated.

Changes can be made to the claimed invention in light of the above Detailed Description. While the above description details certain embodiments of the invention and describes the best mode contemplated, no matter how detailed the above appears in text, the claimed invention can be practiced in many ways. Details of the system may vary considerably in its implementation details, while still being encompassed by the claimed invention disclosed herein.

Particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the claimed invention to the specific embodiments disclosed in the specification, unless the above Detailed Description section explicitly defines such terms. Accordingly, the actual scope of the claimed invention encompasses not only the disclosed embodiments, but also all equivalent ways of practicing or implementing the claimed invention.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." It is further understood that any phrase of the form "A/B" shall mean any one of "A", "B", "A or B", or "A and B". This construct includes the phrase "and/or" itself.

The above specification, examples, and data provide a complete description of the manufacture and use of the claimed invention. Since many embodiments of the claimed invention can be made without departing from the spirit and scope of the disclosure, the invention resides in the claims hereinafter appended. It is further understood that this disclosure is not limited to the disclosed embodiments, but is intended to cover various arrangements included within the spirit and scope of the broadest interpretation so as to encompass all such modifications and equivalent arrangements.

What is claimed is:

1. A urine collection device comprising:
    a body having an internal space for receiving urine;
    a plurality of sensors, each positioned at a different vertical height, with respect to a floor of the body, along a wall of the body;
    wherein the plurality of sensors include different types of sensors, and wherein some of the plurality of sensors are organized in adjacent locations with respect to some other sensors of the plurality of sensors;
    an electronic level device deployed on a rim of the body, parallel to the floor of the body, to detect an orientation of the body and transmit orientation data to be used in computation; and
    a controller to:
        receive data from each of the plurality of sensors and the electronic level device; and
        determine a volume of urine within the body based on the received data and positions of each of the plurality of sensors.

2. The device of claim 1, further comprising:
    a visual display integrated with other components of the urine collection device, the display used to:
        receive the determined volume data from the controller, and
        display a visual representation of the determined volume data.

3. The device of claim 2, where in the rim is attached to the body, the rim being above the body and substantially parallel relative to the floor of the body;
    wherein the visual display is deployed within the rim.

4. The device of claim 1, wherein the different types of sensors include temperature sensors, humidity sensors, and urea sensors.

5. The device of claim 4, wherein determining the volume of urine from the received data includes determining a maximum height for sensors showing an elevated temperature associated with urine and determining a minimum height for sensors showing a non-elevated temperature associated with air.

6. The device of claim 1, wherein the
    plurality of sensors are organized in at least two columns, each of the plurality of sensors in a first of the at least two columns being organized in an adjacent location with respect to a corresponding sensor of the plurality of sensors in a second of the at least two columns, wherein the at least two columns are deployed on the wall of the body and perpendicular to the floor of the body;
    the controller to receive data from each sensor in each of the plurality of sensor columns and to determine the volume of urine from the data received from each sensor column.

7. The device of claim 6, wherein each of the plurality of sensors in the first of the at least two columns is a temperature sensor, and
    wherein the controller is further used to:
        for the first of the at least two columns, determine a maximum height for sensors showing an elevated temperature associated with urine, and determine a minimum height for sensors showing a non-elevated temperature associated with air, and compare the determined heights in each sensor column to determine the volume of urine.

\* \* \* \* \*